United States Patent [19]

Colavito

[11] Patent Number: 5,738,851

[45] Date of Patent: Apr. 14, 1998

[54] METHOD OF REPELLING DEER

[76] Inventor: Rose Anne Colavito, 9 Ninebark La., P.O. Box 162, Oxford, N.J. 07863

[21] Appl. No.: 786,273

[22] Filed: Jan. 22, 1997

[51] Int. Cl.$^6$ ................................................ A61K 35/78
[52] U.S. Cl. .................................................. 424/195.1
[58] Field of Search ........................................ 424/195.1

[56] References Cited

U.S. PATENT DOCUMENTS

| | | | |
|---|---|---|---|
| 4,965,070 | 10/1990 | Messina | 424/581 |
| 5,183,661 | 2/1993 | Messina | 424/405 |
| 5,368,866 | 11/1994 | Loucas | 424/581 |

OTHER PUBLICATIONS

Raver, Anne, *At Long Last Daffodils (Now It Must Be Spring)* The New Yorker.

Wang, S., et al., *Headspace Sampling and Gas Chromatographic–mass Spectrometric Determination of Amphetamine and Methamphetamine in Betel*, Journal of Chromatography A, 715 (1995) 325–331.

Vuorela, H., et al., *Application of Headspace Gas Chromatography in Essential Oil Analysis. VII. Hydrodistillation Compared with Headspace.* Progress in Essential Oil Research, 1986, pp. 551–554.

Loo, Albert et al., *A Study on Narcissus Absolute Composition*, Lawrence, B. M., et al., (Editors) *Flavors and Fragrances: A World Perspective*, Proceedings of the 10th International Congress of Essential Oils, Fragrances and Flavors, Washington, DC, USA., 16–20 Nov. 1986, pp. 355–373.

Umano, Katsumi, et al., *A New Method of Headspace Sampling: Grapefruit Volatiles*, Lawrence, B. et al., (Editors) *Flavors and Fragrances: A World Perspective*, Proceedings of the 10th International Congress of Essential Oils, Fragrances and Flavors, Washington, DC, U.S.A., 16–20 Nov. 1986, pp. 981–998.

Frost, Pam, *Scent Solutions, Scientists Explore New Ways to Make Flower–Friendly Perfumes and Colognes*, Science World, Feb. 10, 1995.

Mookherjee, Braja, et al., *Fruits and Flowers: Live vs. Dead—Which Do We Want?*, Lawrence, B. M., et al., (Editors), *Flavors and Fragrances: A World Perspective*, Proceedings of the 10th International Congress of Essential Oils, Fragrances and Flavors, Washington, DC, USA., 16–20 Nov. 1986, pp. 415–424.

Arnould, Cecile, et al. *Sheep Food Repellents: Efficacy of Various Products. Habituation, and Social Facilitation*, Journal and Chemical Ecology, vol. 19, No. 2, 1993, 1993, pp. 225–236.

*Primary Examiner*—Jean C. Witz
*Attorney, Agent, or Firm*—Eckert Seamans Cherin & Mellott

[57] ABSTRACT

A deer repellant composition is derived from certain plants in the Amaryllidaceae family, using a solvent extraction and concentration method from comminuted plant material, in particular bulbs. Active ingredients extracted by the method are applied by spraying on various types of vegetation, e.g., flowers, plants, food crops, bushes and trees, thereby imparting the taste and/or smell of certain plants in the Amaryllidaceae family to the vegetation, which is thus made unpalatable for discouraging browsing by deer.

16 Claims, 3 Drawing Sheets

METHOD OF REPELLING DEER

BACKGROUND OF THE INVENTION

1. Field of the Invention

The invention relates to an all natural deer repellant composition for discouraging deer from eating foliage. The invention further concerns methods for making the deer repellant composition and methods for applying the same to various types of vegetation, e.g., flowers, plants, food crops, bushes and trees, that are subject to damage by browsing deer.

2. Background

Due to a lack of predators, the population of deer in rural and suburban neighborhoods has increased dramatically. Particularly in communities on the fringes of forested land, populations of deer increasingly forage on landscaped gardens, hedges, etc., resulting in costly and unsightly damage. Deer also forage on saplings and agricultural crops, resulting in losses to timber producers and farmers, respectively.

On the other hand, deer are very appealing animals. It is unpopular to advocate the reduction of deer populations by increased hunting. Increased hunting is also impractical or dangerous in suburban neighborhoods, where deer populations are increasing and the potential for foraging damage is acute.

It would be advantageous if these problems could be remedied short of extermination of the foraging deer, in particular to discourage deer from foraging on ornamental plants and crops, and instead to revert to more natural food. The present invention provides a deer repellant composition that can be applied directly to vegetation to deter browsing by deer, namely by producing a taste and smell naturally associated with unpalatable plants. The composition can be applied to various forms of vegetation without causing stress to the vegetation, and effectively discourages browsing for a period of time.

SUMMARY OF THE INVENTION

It is an aspect of the invention that plants susceptible to browsing damage by deer are protected from such browsing through the topical application of a deer repellant composition, particularly a composition derived from parts of certain plants in the Amaryllidaceae family.

A method is provided for producing a chemical composition useful as a deer repellant. Specifically, a method is provided for producing a deer repellant composition from parts of certain plants in the Amaryllidaceae family, namely Narcissus (common name Daffodil)

Galanthus (common name Snowdrops)

*Amaryllis Belladonna* (common name Naked Lady)

*Chlidanthus Fragrans*

*Crinium x Powellii* (common name Crinium Lily)

*Cyrthanthus Elatus* (common name Scarborough Lily) (also known as *Vallota Purpurea*)

Scadoxus (Haemanthus) Multiflorus (common name Blood Lily)

*Sprekelia Formosissima* (common name Jacobean Lily)

Leucojum (common name Snowflake)

*Nerine Bowdenii & Nerine Sarniensis*

Sternbergia (common name Fall Daffodil)

*Eucharis Amazonica* (common name Amazon Lily)

Hippeastrum (common name Amaryllis)

Hymenocallis (common name Peruvian Daffodil)

Zephyranthus (common name Fairy or Rain Lily)

*Pamianthe Peruviana*

*Phaedranassa Carmioli*

Habranthus preferably

Narcissus (common name Daffodil)

Galanthus (common name Snowdrops)

most preferably

Narcissus (common name Daffodil)

The method includes chopping or otherwise comminuting the plant parts, mixing the chopped product with a solvent, and filtering the resultant mixture to provide a filtrate solution. The deer repellant composition of the invention comprises the filtrate solution which contains the active ingredient or ingredients of the deer repellant.

The method for applying the deer repellant composition to plants susceptible to browsing damage by deer or other ruminants comprises direct application of the composition to the plants in aqueous form. Preferably, the concentrated deer repellant solution is diluted with solvent and sprayed directly onto the vegetation, leaves, flowers, stems and/or bark. The vegetation is thus rendered unpalatable to deer without causing stress to the vegetation.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

DETAILED DESCRIPTION OF THE PREFERRED EMBODIMENTS

The following detailed description is of the best presently contemplated mode of carrying out the invention. The description is not intended in a limiting sense, and it is made solely for the purpose of illustrating the general principles of the invention. The various features and advantages of the present invention may be more readily understood with reference to the following detailed description taken in conjunction with the accompanying drawings.

A chemical composition is provided which may be topically applied to plants to discourage browsing by deer by seeming to render the plants unpalatable. In particular, it is believed that the composition alters the taste and smell characteristics of the plants to which it is applied, causing the deer to associate said plants with certain members of the Amaryllidaceae family, which deer are known not to browse on.

Figure 1:
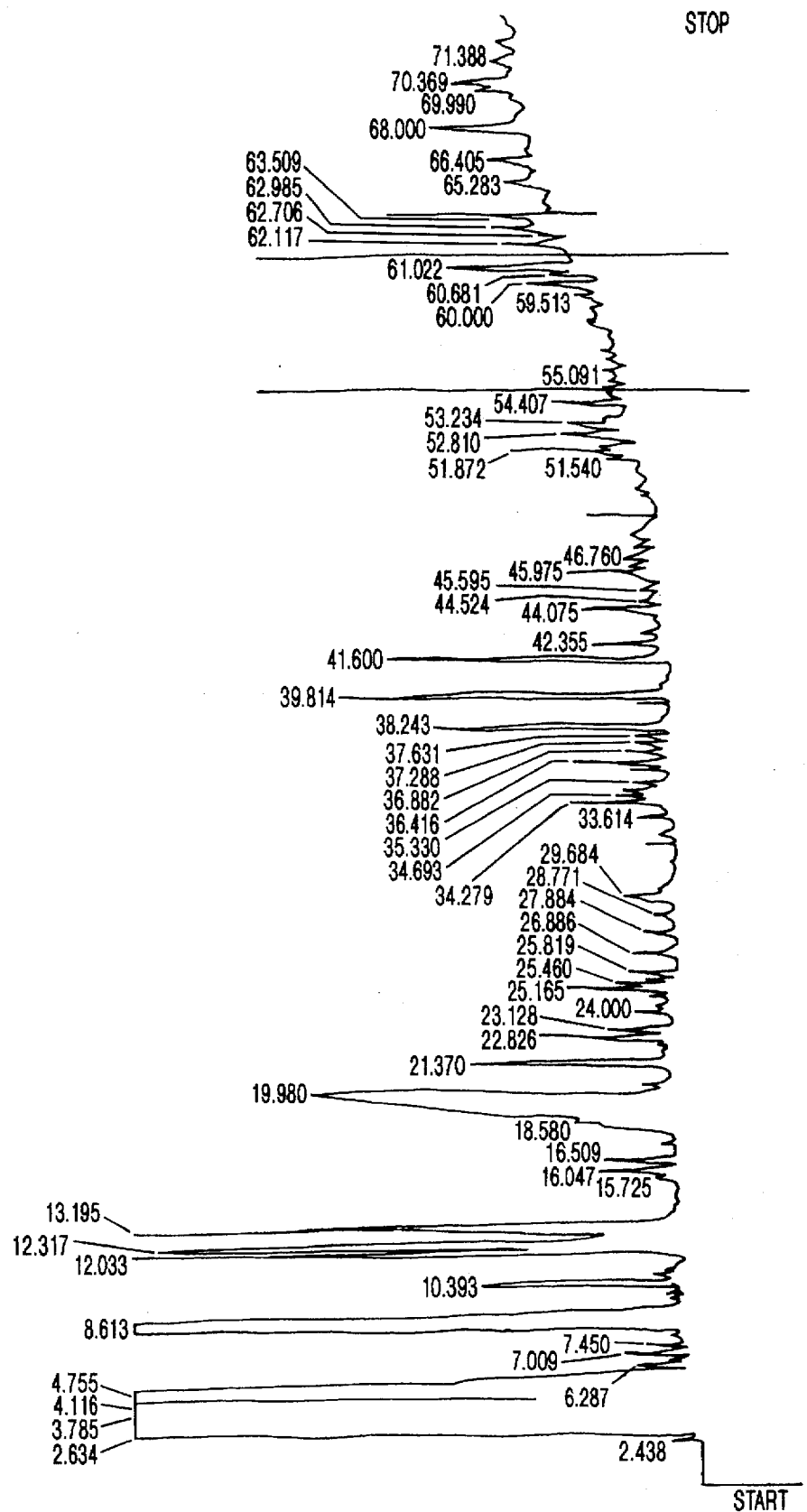
FIG. 1 is a depiction of the gas chromatographic output obtained for a sample of the deer repellant composition derived from Narcissus bulbs using a Hewlett-Packard HP-5890 Gas Chromatograph.

A vapor space extract of a deer repellant composition of the invention derived from Narcissus bulbs was captured in methylene chloride. It is believed that the vapor space extract contains the active ingredient or ingredients which give the deer repellant composition its deer repelling properties. The extract was analyzed using a Hewlett-Packard HP-5890 gas chromatograph and exhibits a characteristic Gas Chromatographic output substantially as shown in FIG. 1.

An inventive method for preparing a deer repellant composition of the invention comprises a series of operations, generally as follows:

(a) comminuting parts of certain plants the Amaryllidaceae family;

(b) mixing the comminuted plant material with a solvent; and, (c) filtering the resultant mixture to provide a solution containing active taste and smell agents, but substantially lacking plant solids.

Certain plants in the Amaryllidaceae family are known to be resistant to foraging by deer and are believed to contain the active ingredient or ingredients that give the deer repellant compositions of the invention their deer repellant properties. In particular, it is believed that the deer repellant compositions of the invention could be derived from any one of the following plants in the Amaryllidaceae family:

Narcissus (common name Daffodil)

Galanthus (common name Snowdrops)

*Amaryllis Belladonna* (common name Naked Lady)

*Chlidanthus Fragrans*

*Crinium x Powellii* (common name Crinium Lily)

*Cyrthanthus Elatus* (common name Scarborough Lily) (also known as *Vallota Purpurea*)

Scadoxus (Haemanthus) Multiflorus (common name Blood Lily)

*Sprekelia Formosissima* (common name Jacobean Lily)

Leucojum (common name Snowflake)

*Nerine Bowdenii & Nerine Sarniensis*

Sternbergia (common name Fall Daffodil)

*Eucharis Amazonica* (common name Amazon Lily)

Hippeastrum (common name Amaryllis)

Hymenocallis (common name Peruvian Daffodil)

Zephyranthus (common name Fairy or Rain Lily)

*Pamianthe Peruviana*

*Phaedranassa Carmioli*

Habranthus preferably

Narcissus (common name Daffodil)

Galanthus (common name Snowdrops)

most preferably

Narcissus (common name Daffodil)

Regardless of the solvent used, the comminuted plant material is preferably mixed with the solvent by subjecting the constituents to vigorous agitation until they are thoroughly mixed. Preferably, the agitation is continued for a period of at least 1 minute. While the use of distilled water is disclosed as preferred, other solvents including organic solvents may be used provided the active ingredient or ingredients are soluble in said organic solvents and said organic solvents are non-toxic to the plants or crops to be treated with the repellant or the animals that might try to consume the treated plants and crops.

The filtrate may be diluted with additional solvent and sprayed directly onto vegetation to be protected from deer browsing using a pump spray bottle or other similar device. The extract may be reapplied as necessary to maintain the deer repellent effect.

The method for making the deer repellant composition of the invention may be further clarified by consideration of the following examples, which are intended to be exemplary and not limiting in nature.

The Narcissus (daffodil) bulbs used in the following examples were "Dutch Master" and "King Alfred" Trumpet Type Division I variety. Comminution and mixing was accomplished using a kitchen knife and an Osterizer Blender model Touch-A-Matic 14 Dual Range, manufactured by Hamilton Beach. Cheese cloth was used as the filter element for filtering the mixed plant solids and solvent. Cheese cloth is commercially available from Cadie Prod. Corp., Paterson, N.J. under the designation Finest Quality Cheese Cloth.

Example 1

About 82.5 g dormant daffodil bulbs were chopped with a knife and added to about 600 ml of distilled water. The combination was mixed in an Osterizer Blender on "High" using the "Grind" setting for about 1 minute, thereby further comminuting the plant solids as well as mixing the plant material with the water. The mixture was then filtered through 4 layers of cheese cloth. The filtrate solution was collected and transferred to a 1000 ml erlenmeyer flask. A 325 ml portion of the filtrate was poured into a spray bottle and applied to one section of a field of clover subject to browsing by deer. The field of clover was subsequently observed over a period of weeks. The treated clover was found to be significantly less foraged by deer than the neighboring control area of untreated clover.

Narcissus and Galanthus contain the alkaloid Lycorine, which is a known poison. Tests were done to demonstrate that the deer repellant compositions of the invention do not owe their effectiveness to lycorine. First, a vapor space extract of a deer repellant composition of the invention derived from Narcissus bulbs was captured in methylene chloride. The vapor space extract was analyzed using a Hewlett-Packard HP-5890 Series II gas chromatograph coupled with a HP-5971 Series mass selective detector operated in full scan mode. The results of that analysis demonstrated that the vapor space extract of the deer repellant composition did not contain lycorine.

Figure 2:
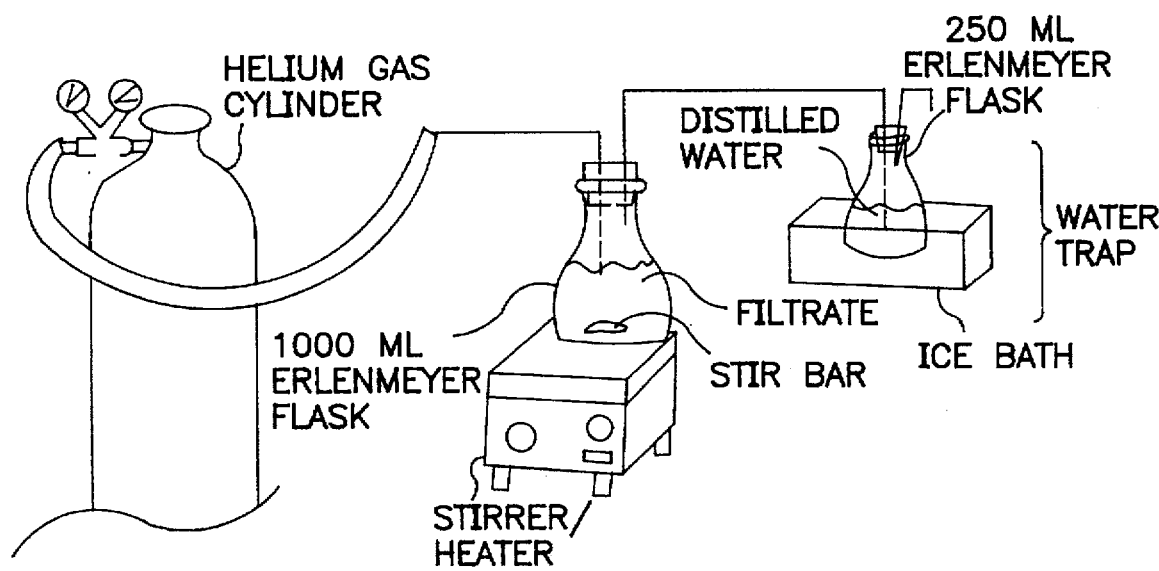
FIG. 2 is a depiction of a first apparatus for extracting active agents from the filtrate; and, FIG. 3 is a depiction of an alternative apparatus for extracting said active agents.
Figure 3:
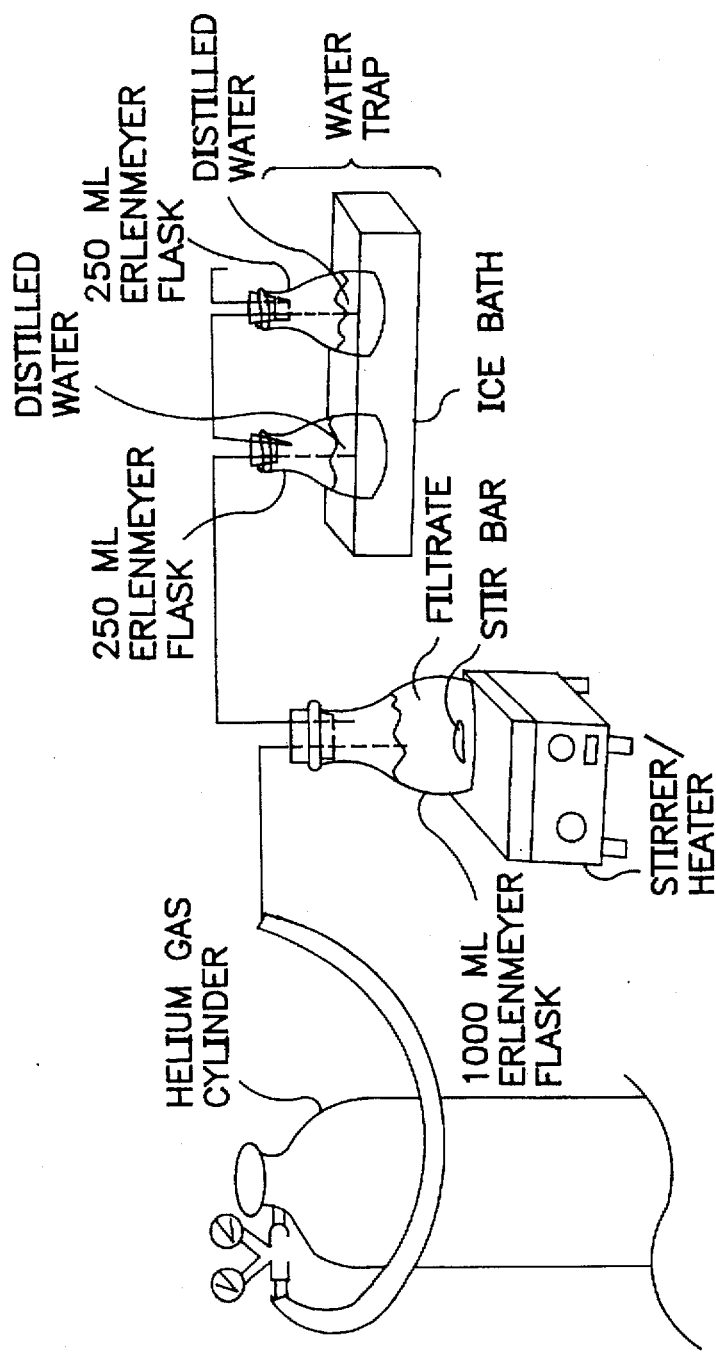

Second, vapor space extracts from the deer repellant compositions of the invention were obtained with an apparatus similar to that shown in FIG. 2 or FIG. 3 using the following procedure:

(a) sparging helium through the filtrate solution, while subjecting the filtrate solution to constant agitation and optionally with heat; and, (b) passing the sparged helium through a solvent trap maintained at about the freezing point temperature of water to extract the active agents of the product composition from the sparged helium.

These vapor space extracts were then applied to foliage to observe whether they exhibited deer repellant properties. The following examples describe the specific tests performed in greater detail.

Example 2

About 82.5 g dormant daffodil bulbs were chopped with a knife and added to about 600 ml of distilled water. The combination was mixed in an Osterizer Blender on "High" using the "Grind" setting for about 1 minute, thereby further comminuting the plant solids as well as mixing the plant material with the water. The mixture was then filtered through 4 layers of cheese cloth. The filtrate solution was collected and transferred to a 1000 ml erlenmeyer flask. A 2"

stir bar was added to the flask and the filtrate was subjected to agitation using a THERMOLYNE Type 1000 Series 463 stirrer/heat plate with the agitator speed dial set a ½ full speed (approximately 500 rpm). Helium gas was bubbled through the filtrate and into about 225 ml of distilled water contained in a 250 ml erlenmeyer flask located in an ice bath. The apparatus used is generally depicted in FIG. 2. The gas bubbling continued for about 3 hours. The active ingredient captured in the 225 ml water trap was diluted with an additional 100 ml of distilled water to provide 325 ml of repellant. The 325 ml was poured into a spray bottle and applied to one section of a field of clover subject to browsing by deer. The field of clover was subsequently observed over a period of weeks. The treated clover was found to be less significantly foraged by deer than the neighboring control area of untreated clover.

Example 3

The test used in Example 1 was repeated with similar results using an extract produced using the following process. Daffodil bulbs were chopped with a knife. About 82.5 g of the chopped daffodil bulbs were added to about 600 ml of distilled water. The combination was mixed in an Osterizer Blender on "High" using the "Grind" setting for about 1 minute. The mixture was then filtered through 4 layers of cheese cloth. The filtrate was collected and transferred to a 1000 ml erlenmeyer flask. A 2" stir bar was added to the flask and the filtrate was subjected to agitation using a THERMOLYNE Type 1000 Series 463 stirrer/heat plate with the agitator dial set at ½ full speed and with the heater dial set at 1. Using the same apparatus used in Example 1, helium gas was bubbled through the filtrate into about 225 ml of distilled water contained in a 250 ml erlenmeyer flask located in an ice bath. The gas bubbling continued for about 6 hours. The active ingredient captured in the 225 ml water trap was diluted with an additional 100 ml of distilled water to provide about 325 ml of deer repellant.

Example 4

The test used in Example 1 was repeated with more promising results using an extract produced using the following process. Daffodil bulbs were chopped with a knife. About 82.5 g of the chopped daffodil bulbs were added to about 600 ml of distilled water. The combination was mixed in an Osterizer Blender on "High" using the "Grind" setting for about 1 minute. The mixture was then filtered through 4 layers of cheese cloth. The filtrate was collected and transferred to a 1000 ml erlenmeyer flask. A 2" stir bar was added to the flask and the filtrate was subjected to agitation using a THERMOLYNE Type 1000 Series 463 stirrer/heat plate with the agitator dial set at ½ full speed and the heater dial set at 1. Helium gas was bubbled through the filtrate into about 225 ml of distilled water contained in a first 250 ml erlenmeyer flask located in an ice bath. The Helium, with any entrained gases, passing through the 225 ml water trap was bubbled through about 100 ml of distilled water contained in a second 250 ml erlenmeyer flask connected in series with the first and also located in an ice bath. The apparatus used is generally depicted in FIG. 3. The gas bubbling continued for about 12 hours. The contents of the two 250 ml erlenmeyer flasks were combined to provide about 325 ml of deer repellant.

Example 5

About 170 g daffodil bulbs were chopped with a knife and were added to about 900 ml of distilled water. The combination was mixed in an Osterizer Blender on "High" using the "Grind" setting for about 1 minute. The mixture was then filtered through 4 layers of cheese cloth. The filtrate was collected and transferred to a 1000 ml erlenmeyer flask. A 2" stir bar was added to the flask and the filtrate was subjected to agitation using a THERMOLYNE Type 1000 Series 463 stirrer/heat plate with the agitator dial set at ½ full speed and with the heater dial set at 1. Helium gas was bubbled through the filtrate into about 1000 ml of distilled water contained in a 1000 ml erlenmeyer flask and then into 200 ml of distilled water in a 225 ml flask. Both the 1000 ml flask and the 225 ml flask were located in an ice bath. The gas bubbling continued for about 6 hours. The active ingredient captured in both the 1000 ml flask and the 225 ml flask was combined to provide 1200 ml of repellant.

Previous observations of the deer herd populating the vicinity of the test site demonstrated a proclivity for grazing on hosta plants. To test the effectiveness of the repellant of the invention for repelling grazing deer four hosta plants, two untreated and two treated, were placed at the test site and observed. The treated plants were treated using the deer repellant composition of the invention as described above, namely by spraying the composition derived from the above process onto the hosta plant leaves and stalks. The site was surveyed on a daily basis. All four plants remained substantially untouched during the first three days. By the fourth day, while the plants treated with the deer repellant showed signs of only minor browsing or nibbling by deer, the untreated plants showed signs of significant foraging with about one-half to two-thirds of their leaves browsed off by deer.

It is believed that the foregoing aqueous process is preferable over volatile solvents. Notwithstanding, organic solvents may prove effective for use with the invention. In addition, it has been found that direct application of Narcissus plant material solids tends to stress the plants. The aqueous process as described provides a means to extract sufficient active ingredients to obtain beneficial deer repellant effects, without unduly stressing the plants.

While certain present preferred embodiments of the invention have been illustrated and described, it is to be understood that the invention is not limited thereto and may be otherwise practiced within the scope of the following claims.

We claim:

1. A method for protecting foliage from browsing by deer, comprising spraying on the foliage an effective amount of a deer repellant with an active agent or agents having a gas chromatographic output substantially as shown in FIG. 1.

2. A method for protecting foliage from browsing by deer, comprising spraying on the foliage an effective amount of a deer repellant obtained from plants selected from the group of Amaryllidaceae consisting of Narcissus (common name Daffodil), *Amaryllis Belladona* (common name Naked Lady), *Crinium x Powellii* (common name Crinium Lily), *Cyrthanthus Elatus* (also known as *Vallota Purpurea*; common name Scarborough Lily), Scadoxus (Haemanthus) Multiflorus (common name Blood Lily), *Sprekelia Formosisium* (common name Jacobean Lily), *Nerine Bowdenii, Nerine Sarniensis, Eucharis Amazonica* (common name Fairy or Rain Lily), Galanthus (common name Snowdrops), *Chlidanthus Fragrans*, Leucojum (common name Snowflake), Sternbergia (common name Fall Daffodil), Hippeastrum (common name Amaryllis), Hymenocallis (common name Peruvian Daffodil), *Pamianthe Peruviana, Phaedranassa Carmioli*, and Habranthus.

3. The method of claim 2, wherein the plants are selected from the group of Amaryllidaceae consisting of Narcissus and Galanthus.

4. The method of claim 2, wherein the deer repellant is obtained from Narcissus.

5. The method of claim 2, wherein the deer repellant is obtained from Narcissus bulbs.

6. A method for protecting foliage from browsing by deer, comprising spraying on the foliage an effective amount of a deer repellant produced by:

(a) comminuting plants selected from the group of Amaryllidaceae consisting of Narcissus (common name Daffodil), *Amaryllis Belladona* (common name Naked Lady), *Crinium x Powellii* (common name Crinium Lily), *Cyrthanthus Elatus* (also known as *Vallota Purpurea*; common name Scarborough Lily), Scadoxus (Haemanthus) Multiflorus (common name Blood Lily), *Sprekelia Formosisium* (common name Jacobean Lily), *Nerine Bowdenii, Nerine Sarniensis, Eucharis Amazonica* (common name Fairy or Rain Lily), Galanthus (common name Snowdrops), *Chlidanthus Fragrans*, Leucojum (common name Snowflake), Sternbergia (common name Fall Daffodil), Hippeastrum (common name Amaryllis), Hymenocallis (common name Peruvian Daffodil), *Pamianthe Peruviana, Phaedranassa Carmioli*, and Habranthus, (b) mixing the comminuted plants with a solvent, (c) filtering the resultant mixture, and (d) collected the filtrate.

7. The method of claim 6, wherein the plants are selected from the group of Amaryllidaceae consisting of Narcissus and Galanthus.

8. The method of claim 6, wherein the plants are Narcissus.

9. The method of claim 8, wherein the plants are Narcissus bulbs.

10. The method of claim 6, wherein the solvent is selected from the group consisting of organic and aqueous solvents.

11. The method of claim 6, wherein the solvent is water.

12. The method of claim 6, wherein the solvent is distilled water.

13. The method of claim 6, wherein step (b) is accomplished using vigorous agitation for a period of at least 1 minute.

14. A method for protecting foliage from browsing by deer, comprising spraying on the foliage an effective amount of a deer repellant produced by:

(a) comminuting Narcissus bulbs, (b) mixing the comminuted plants with a solvent, (c) filtering the resultant mixture, and (d) collected the filtrate.

15. The method of claim 14, wherein the Narcissus bulbs are selected from the group consisting of "Dutch Master" and "King Alfred" Trumpet Type Division I variety.

16. The method of claim 14, wherein step (b) is accomplished using vigorous agitation for a period of at least 1 minute.

* * * * *

UNITED STATES PATENT AND TRADEMARK OFFICE
CERTIFICATE OF CORRECTION

PATENT NO. : 5,738,851
DATED : April 14, 1998
INVENTOR(S) : Rose Anne Colavito

It is certified that error appears in the above-identified patent and that said Letters Patent is hereby corrected as shown below:

Column 6, Claim 2, line 58, after "Amazonica", insert --(common name Amazon Lily), Zephyranthus--.

Column 7, Claim 6, line 17, after "amazonica", insert --(common name Amazon Lily), Zephyranthus--.

Column 7, Claim 6, line 27, delete "collected", and substitute therefor --collecting--.

Column 8, Claim 14, line 22, delete "collected" and substitute therefor --collecting--.

Signed and Sealed this

Nineteenth Day of January, 1999

Attest:

Attesting Officer

*Acting Commissioner of Patents and Trademarks*